United States Patent
Gottlieb et al.

(10) Patent No.: US 10,765,836 B1
(45) Date of Patent: Sep. 8, 2020

(54) ELECTRONIC GUIDEWIRE DETECTOR FOR CATHETER INSERTION

(71) Applicant: HORIZON PATENTS, LLC., Fairfax Station, VA (US)

(72) Inventors: Mark M. Gottlieb, Fairfax Station, VA (US); James B. Solomon, Vienna, VA (US)

(73) Assignee: HORIZON PATENTS, LLC., Fairfax Station, VA (US)

( * ) Notice: Subject to any disclaimer, the term of this patent is extended or adjusted under 35 U.S.C. 154(b) by 0 days.

(21) Appl. No.: 16/368,464

(22) Filed: Mar. 28, 2019

(51) Int. Cl.
*A61M 25/09* (2006.01)
*A61M 25/01* (2006.01)

(52) U.S. Cl.
CPC ........ *A61M 25/09* (2013.01); *A61M 25/0127* (2013.01); *A61M 2025/0166* (2013.01); *A61M 2205/3306* (2013.01); *A61M 2205/50* (2013.01); *A61M 2205/581* (2013.01); *A61M 2205/584* (2013.01); *A61M 2205/587* (2013.01); *A61M 2210/12* (2013.01)

(58) Field of Classification Search
CPC .............. A61M 25/09; A61M 25/0127; A61M 2025/0166; A61M 2210/12; A61M 2205/50; A61M 2205/3306; A61M 2205/587; A61M 2205/581; A61M 2205/584

USPC ...................................................... 340/686.1
See application file for complete search history.

(56) References Cited

U.S. PATENT DOCUMENTS

| | | | | |
|---|---|---|---|---|
| 2010/0210934 A1* | 8/2010 | Belson | ............. | A61M 25/0105 600/371 |
| 2011/0046477 A1* | 2/2011 | Hulvershorn | ........ | A61B 5/0215 600/424 |
| 2013/0281787 A1* | 10/2013 | Avneri | ............. | A61M 25/0133 600/208 |
| 2017/0290547 A1* | 10/2017 | Levine | ................. | A61B 8/5223 |
| 2017/0372640 A1* | 12/2017 | Lampotang | ............. | G09B 9/00 |
| 2018/0279909 A1* | 10/2018 | Noonan | ................. | A61B 90/37 |

* cited by examiner

*Primary Examiner* — Hirdepal Singh
(74) *Attorney, Agent, or Firm* — Oblon, McClelland, Maier & Neustadt, L.L.P.

(57) ABSTRACT

A detector and a method of its use with a guidewire to reduce the incidence of guidewires accidently being left inside patients during the placement of central venous (and other) catheters. In particular, an electronic detector detects whether a catheter has been placed over a guidewire and whether the guidewire has been removed thereafter. In addition, the distance the guidewire has progressed out the patient side of the detector housing which will correspond to the length of guidewire actually inside the patient and any time may be provided.

21 Claims, 14 Drawing Sheets

Non-Tunneled Central Venous Access Device

ELECTRONIC GUIDEWIRE DETECTOR FOR CATHETER INSERTION

FIELD OF INVENTION

The present invention is directed to a detecting the presence of a guidewire for use with a catheter, and, in one embodiment, to a detector for detecting that a guidewire for use with a central venous catheter (CVC) has been accidentally left in place during a medical procedure or operation.

DISCUSSION OF THE BACKGROUND

A "central venous catheter" (CVC), also known as a "central line," "central venous line," or "central venous access catheter," is a catheter placed into a large vein. Catheters, such as the known 3 lumen catheter of FIG. 1, can be placed in veins in the neck (internal jugular vein), chest (subclavian vein or axillary vein), groin (femoral vein), or through veins in the arms (also known as a peripherally inserted central catheters (PICC) line). It is used to administer medication or fluids that are unable to be taken by mouth or would harm a smaller peripheral vein, obtain blood tests (specifically the "central venous oxygen saturation"), and to measure central venous pressure. FIGS. 2A and 2B illustrate catheters having been inserted into patients. FIG. 3A illustrates a three lumen (or three-segment) catheter that has corresponding caps for closing off the "ports" or openings of the catheter.

More than 50 million surgical procedures were performed in the United States. As part of some of those procedures, central venous catheters are inserted into patients. Before a catheter is placed into a patient, a guidewire must be inserted in the blood vessel to act as a guide for the catheter. The guidewire has become an integral part of a growing number of medical procedures with its use steadily increasing and expanding into more and more medical specialties, particularly as non-invasive procedures have been developed. The market for guidewires is now global and growing. Market data shows this market to be about $1 billion globally each year and growing at a CAGR of 8.2%.

A guidewire is a thin, flexible, medical wire inserted into the body to guide a larger instrument, such as a catheter, central venous line, or feeding tube. The materials used to make guidewires have varied over the years but today they primarily consist of stainless steel and Nitinol (nickel titanium). Not all of a guidewire is placed into a patient as the guidewire must be retrievable after insertion of the catheter. As used herein, the phrase "the patient side of the guidewire" will be used to refer to at least the end of the guidewire that is inserted into the patient. The other end will be called "the caregiver end".

As discussed above, during placement of a central venous catheter, the blood vessel is penetrated with a hollow needle and a guidewire is then advanced through the needle into the vessel. The needle is removed, leaving the wire in place, and the catheter is advanced over exposed or caregiver end of the guidewire until the first part or caregiver end of the wire extends outside the back of the catheter. Then, while holding the wire in place so that it does not move, the catheter is advanced into proper position within the vessel. Once the catheter is in place the guidewire is grabbed by the caregiver side and removed and discarded—leaving the catheter in place.

The most common complications of central venous catheters are infection and damage to surrounding structures. A less common but more serious complication is the accidental failure to remove the guidewire after placement and at times after the operation is complete—leaving the guidewire fully retained within the body. Despite the rare occurrence (approx. 1 per 3,000 placements), these retained guidewires cause significant potential harm to the patient including more surgeries, more lengthy hospital stays, additional medical problems, and potentially death. That 1:3,000 number correlates to over 2,000 occurrences annually in the US alone. Mortality rates with retained guidewires is as high as 1 in 5.

There are detailed procedures in place to assure that guidewires are never inadvertently left in patients. These include checklists, instrument counts, and careful training. Nonetheless, these events continue to happen due to human error. The most common cause is catheter advancement into the body over the wire before the guidewire is threaded the entire length of the catheter so that the lagging or caregiver end of the wire can be gripped by the user and held in place during advancement. Consistent factors noted in many investigations include operator fatigue, distractions, emergency situations, and inexperience. These human factors cause safety steps to be forgotten or skipped in the interest of expediency or deviated from due a confluence of uncommon events. Almost all safety steps in place require the operator to perform various safety checklists even though human factors often reduce their reliability. Very little safety engineering has been done to modify equipment and reduce the potential for human error.

An exemplary set of steps for installing a known catheter is provided below. (The same or similar procedures are used for many other types of operations in which a guidewire is used to place a catheter.)

1. A needle is inserted into the blood vessel at a location on the body where the catheter is to be placed.
2. Guidewire is pushed through the needle into the blood vessel.
3. Guidewire continues to be pushed into the blood vessel to the appropriate depth so that the guidewire remains in the vessel once the needle is removed.
4. The needle is removed over the exposed or caregiver end of the guidewire while leaving the guidewire in place.
5. A catheter is advanced over the exposed or caregiver end of the guidewire and into position so that the leading tip of the catheter is completely in the blood vessel.
6. The guidewire is grabbed by its caregiver end and removed through the catheter and discarded, leaving the catheter in proper position.
7. The catheter is secured in place with sutures and/or adhesive dressing to maintain proper position.

BRIEF DESCRIPTION OF THE DRAWINGS

The following description, given with respect to the attached drawings, may be better understood with reference to the non-limiting examples of the drawings, wherein.

DISCUSSION OF THE PREFERRED EMBODIMENTS

Figure 1:
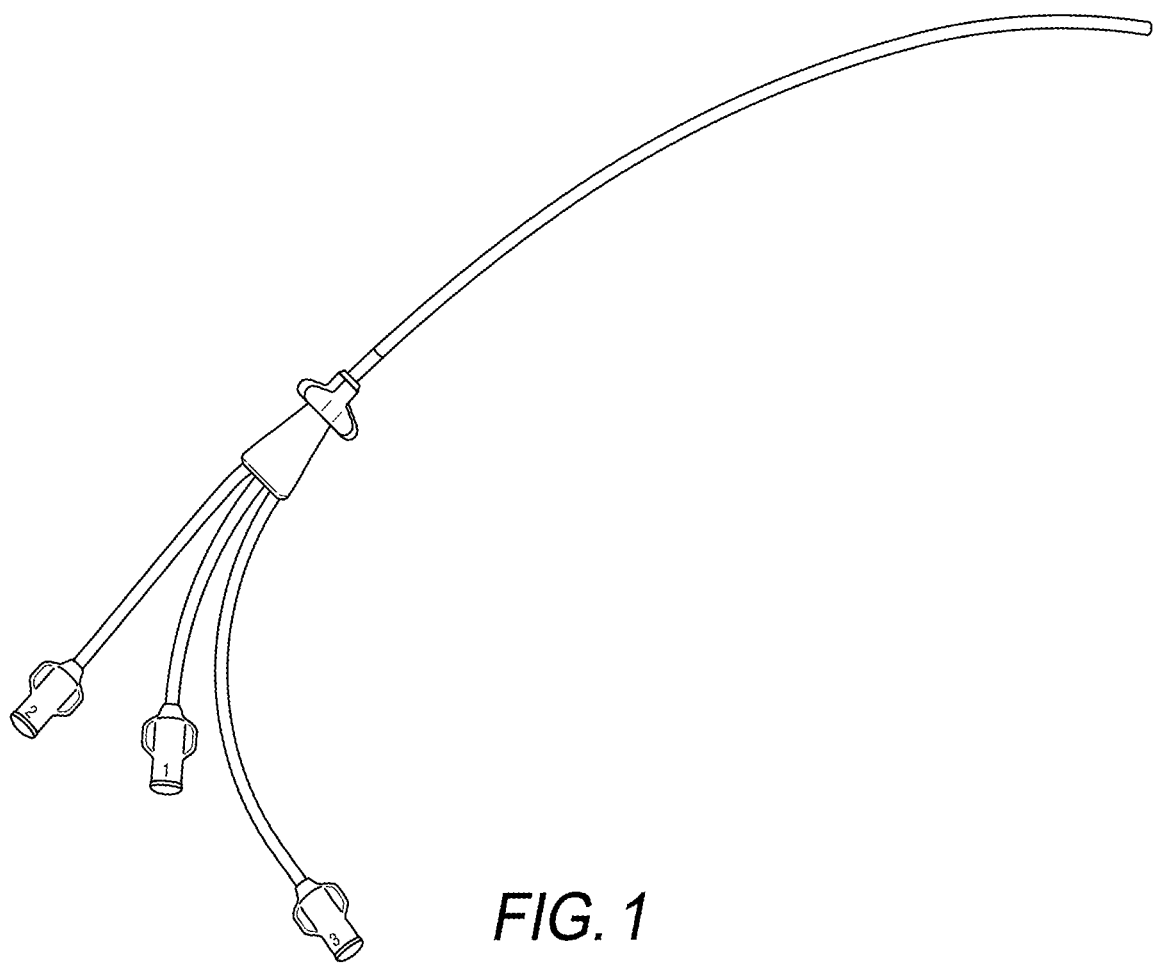
FIG. 1 is an illustration of an exemplary, known 3 lumen catheter prior to insertion into a patient.
Figure 2A:
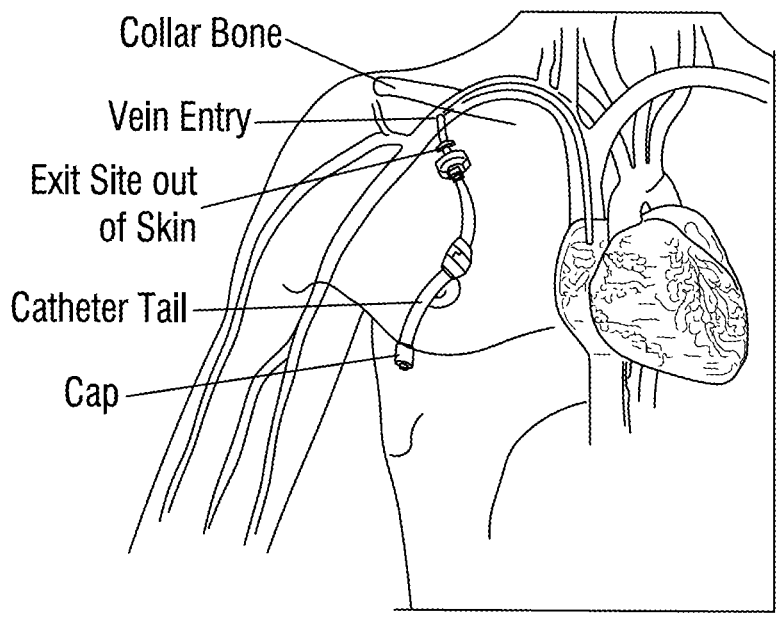
FIG. 2A is an illustration of a catheter as used when inserted into a patient.
Figure 2B:
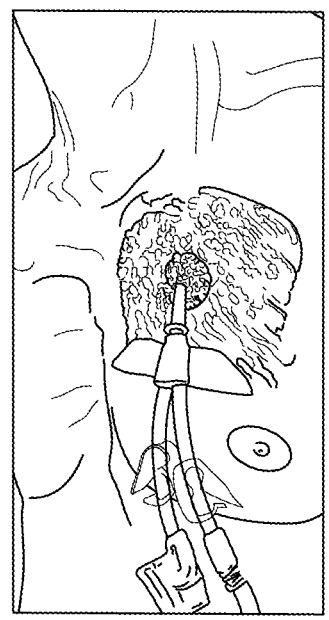
FIG. 2B is a picture of a patient into whom a catheter has been inserted.
Figure 3A:
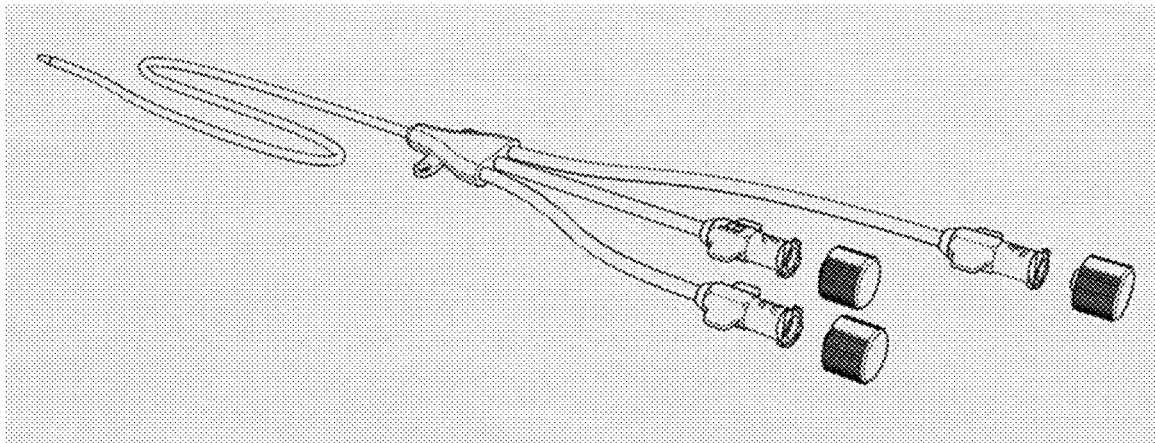
FIG. 3A is an illustration of a 3 lumen catheter with its corresponding caps for closing off the ports of the catheter.
Figure 3B:
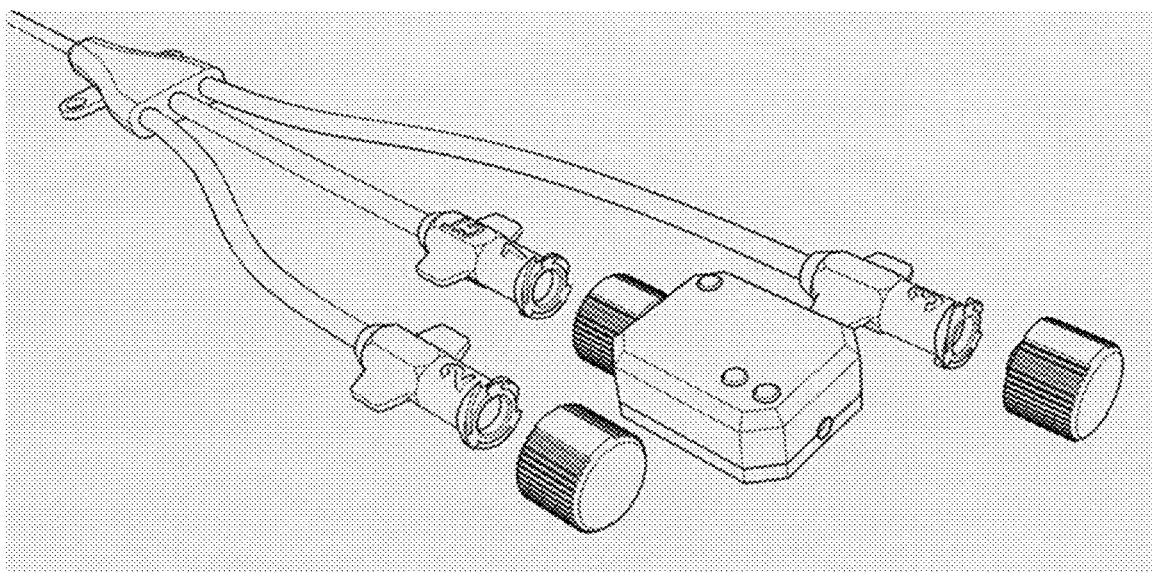
FIG. 3B is an illustration of a 3 lumen catheter where one of the caps has been replaced with a detector according to a first embodiment of the invention.

The present invention is directed to a design of a detector for use with a guidewire to reduce the incidence of guidewires accidently being left inside patients after the placement of central venous (and other) catheters and/or left inside a patient after removal of the catheter (at the end of an operation or other medical procedure). In particular, a detector can be placed on or integrated with a portion of a catheter to detect the presence and/or removal of a guidewire. The detector can provide doctors, nurses and/or other medical professionals with at least one of a visual indication or an audible indication of the location of the guidewire relative to a reference point (e.g., a location close to a port or the port hub) of the catheter. As shown in FIG. 3B, the detector can be created in the form of a larger cap for one of the ports (e.g., the red port ('distal port')). Alternatively, the detector could be incorporated into this plastic port hub (Y-Connector) without departing from the teachings herein.

Figure 4A:
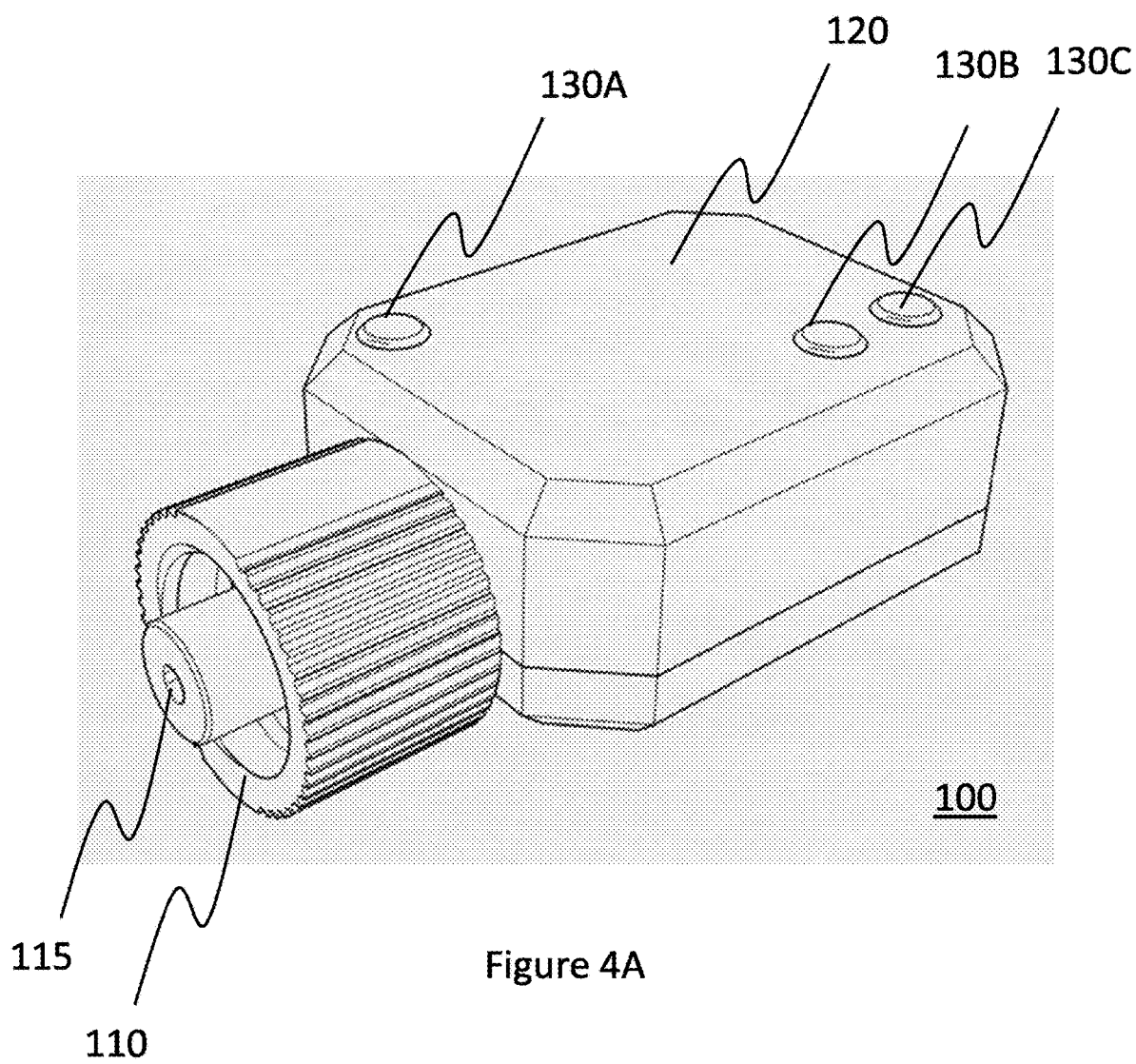
FIG. 4A is a perspective view of the detector of FIG. 3B where the cover of the detector surrounds the internal circuitry of the detector.
Figure 4B:
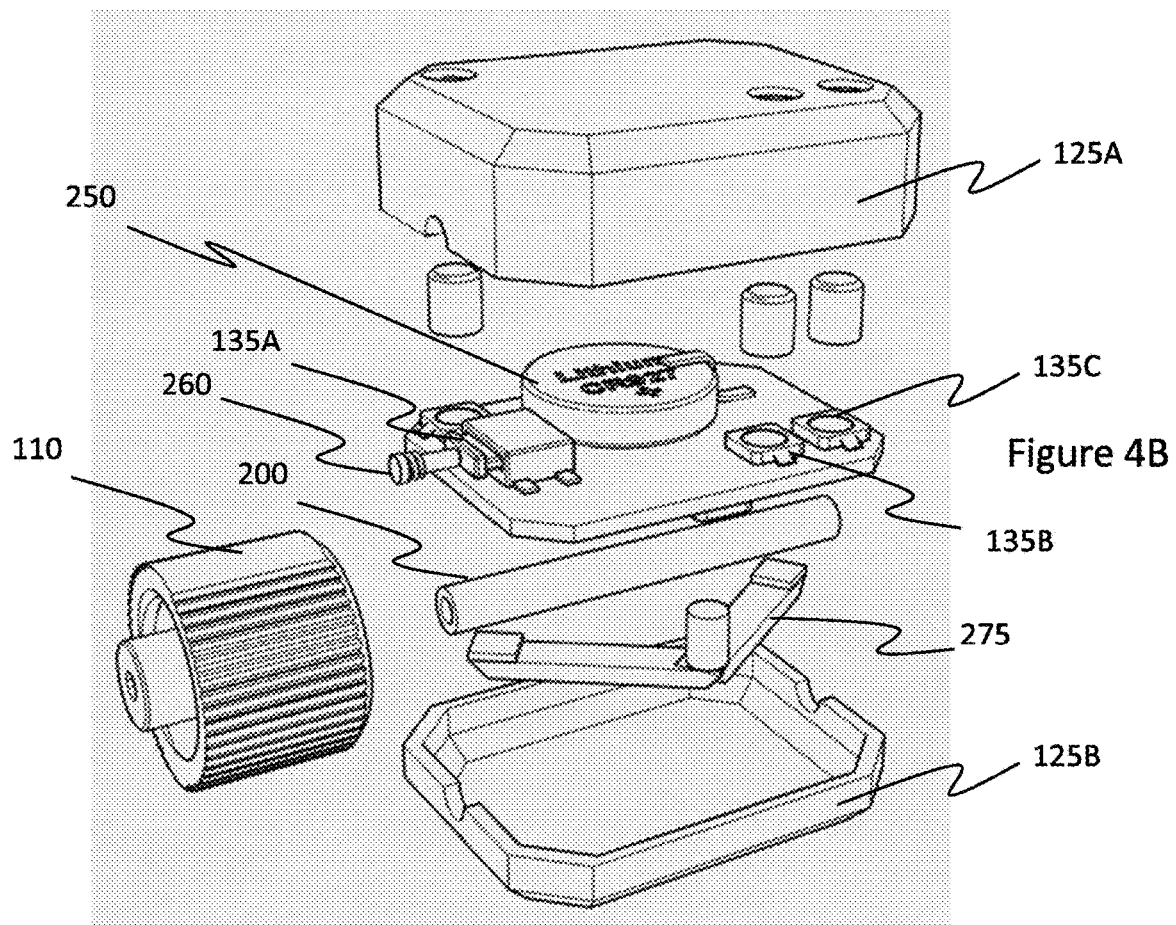
FIG. 4B is a partial exploded side view of the detector.
Figure 4C:
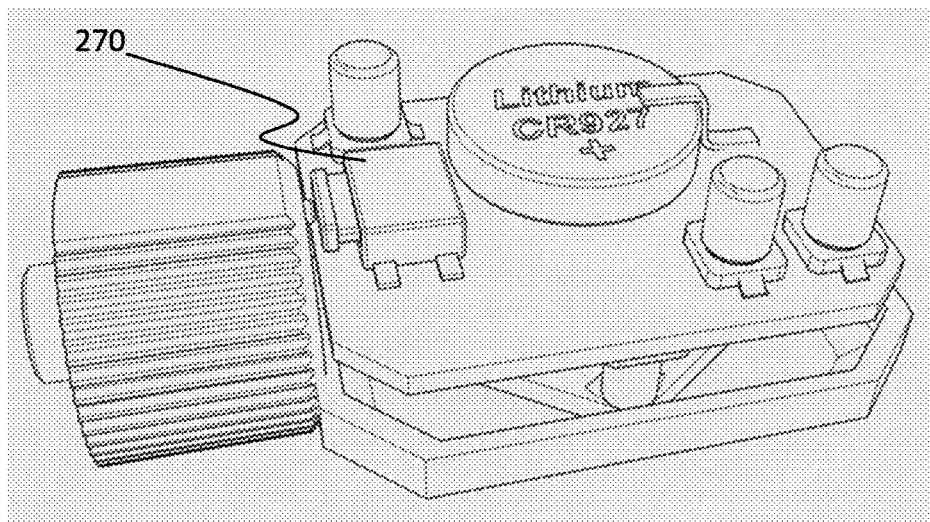
FIG. 4C is a top view of the detector of FIG. 4A where the cover of the detector has been removed for illustrative purposes to expose the internal circuitry.

One illustrative embodiment of the detector 100 described herein is illustrated in FIG. 4A. The detector 100 includes a cap 110 for connecting to the catheter but providing a guidewire passage 115 there through. The detector 100 further includes a housing 120 mechanically connected to the cap 110 that surrounds the internal circuitry of the detector 110. In the illustrated embodiment, the housing 120 also has three illumination sections (130A-130C) which allow a number of conditions detected by the detector 110 to be indicated to the medical professionals utilizing the detector 100. Illumination sections 130A-130C can be of the same or different types and can include, but are not limited to, (a) windows for allowing lights from interior bulbs or LEDs to be seen from outside the housing 120, (b) bulbs, or (c) LEDs. Each illumination section can be of a single color or multiple colors to indicate a number of conditions as discussed below. The conditions may be indicated by turning on and off illumination sections, and/or by changing a frequency of blinking of illumination sections. Alternatively, or in addition to the illumination sections, the detector 100 may include a speaker (e.g., a piezoelectric speaker) (not shown) for audibly indicating one or more conditions.

In general, the detector 100 can detect and indicate to the medical professionals a number of conditions for a guidewire initially inserted into the catheter either from the patient side or the caregiver side. Starting with a guidewire inserted initially from the caregiver side, the detector 100 can sense conditions including, but not limited to: (1) the guidewire has not yet been inserted through the housing, (2) the guidewire has been inserted through the housing but has not yet been removed through the housing, (3) the guidewire has been both inserted through the housing and properly removed from the housing, (4) the guidewire has been inserted through the housing but has moved into an unsafe location, and (5) the guidewire has been inserted through the housing but has been left in the patient—i.e. it has not returned out the correct side. The conditions can be indicated using one or more illuminations sections and/or a speaker. In addition to light and audible notifications—the system could include a small digital display that could show the length of guidewire that is in the body at any given time.

Figure 5A:
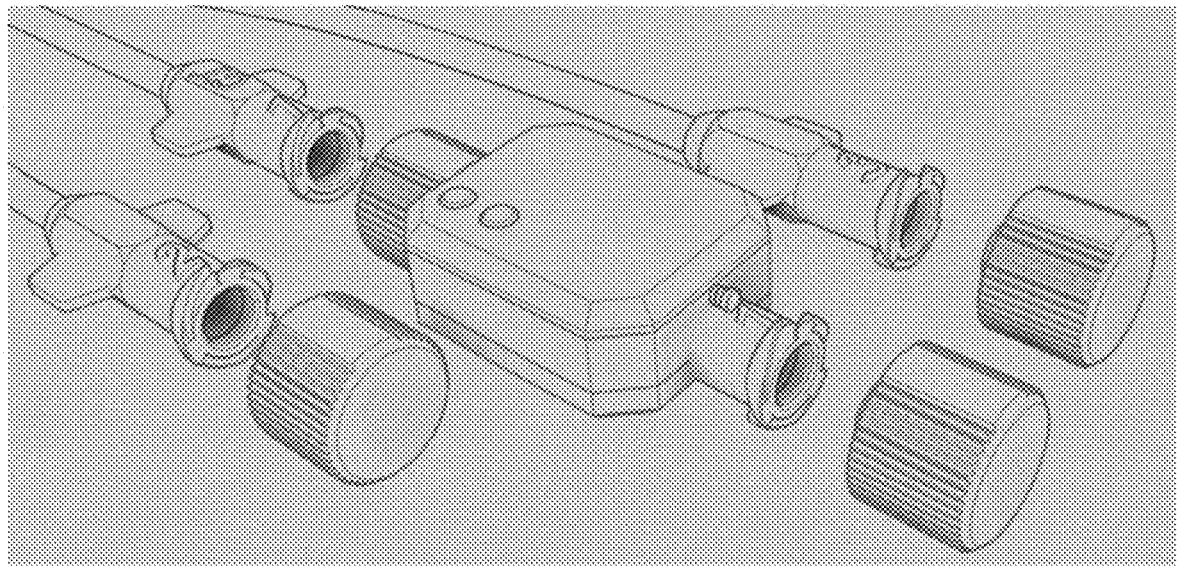
FIG. 5A is an illustration of a detector according to a second embodiment described herein.
Figure 5B:
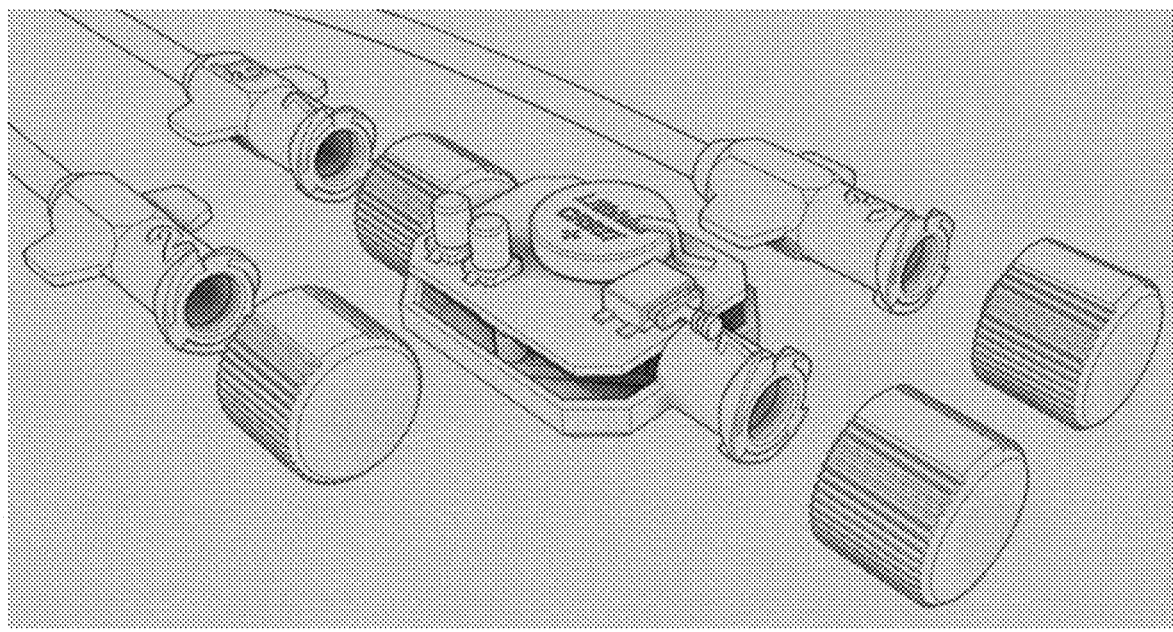
FIG. 5B is a partially exposed view of the circuit board inside the housing of the detector of FIG. 5B.

For example, in a first embodiment with two illuminations sections 130B and 130C (e.g., as shown in FIGS. 5A and 5B) corresponding to red and green LEDs, respectively, the detector indicates when the guide wire is in each of three locations by illuminating the LEDs according to:
 (Red off, Green off): Guidewire not inserted yet or inserted and properly removed;
 (Red off, Green on): Guidewire has been inserted and not yet properly removed and has not moved into an unsafe position (e.g., the caregiver-side end of the guidewire has entered into the detector)
 (Red on, Green off): Guidewire has gone too far and is now past the last of all the sensors in the detector and fully on the body side of the detector such that there is potentially a problem.

In a second embodiment with two illuminations sections 130B and 130C corresponding to red and green LEDs, respectively, and a speaker, the detector indicates when the guide wire is in each of four locations by illuminating the LEDs and utilizing the speaker according to:
 (Red off, Green off): Guidewire not inserted yet or inserted and properly removed;
 (Red off, Green on): Guidewire has been inserted and not yet properly removed and has could have moved into an unsafe position (e.g., the caregiver-side end of the guidewire has entered into the detector to a point beyond the first of at least three sensors in the detector)

(Red flashing, Green on, speaker beeping): Guidewire has gone nearly too far and is now in danger of going fully on the body side (e.g., to a point beyond at least two sensors of at least three sensors but has not gone beyond the last sensor).

(Red on, Green on, speaker on continuous tone): Guidewire has gone too far and is now fully on the body side and potentially fully into the body (e.g., to a point beyond the last sensor of the detector).

To further aid in preventing the guidewire from going too far into the patient, the detector may include a grabbing mechanism (e.g., a spring-loaded pinching device or a metal that changes shape when electricity is applied to it) that can be triggered in one or both of either of the last two states described above. In such a configuration, the detector would attempt to "grab" the guidewire before it is no longer within the detector. Such a grabbing device may be placed inside the tube in which the guidewire is passing or adjacent to the tube but having sufficient force to alter the shape of the tube such that the guidewire is grabbed.

In a third embodiment, the detector includes a display (e.g., such a 7 or 9 segment LED digit display, an LCD with back-light, or a number of LED bars) (not shown) and further includes a detector for determining (and displaying the distance the guidewire has been advanced through the detector. This has many practical applications to the doctor placing the wire, helping them gauge the distance the wire is now in the body. By knowing the distance, the doctor can put the wire in to the exact length of the catheter—without having to over compensate. It is always better to have just enough length in the body but not too much as the extra length only adds to the potential for unnecessary puncture of the vein wall during insertion. Pushing the guidewire in unnecessarily far also could lead to disruption of the heart's normal rhythm. In such a configuration, the display can give an actual distance of the length traveled by the guidewire, and the detector can give a warning (e.g., an audible alarm, a flashing of the display, or a change in the back-light color) when the guidewire is getting too close to the end.

In a fourth embodiment, the detector includes red and green LEDs 130B and 130C where the red LED 130B turns on upon power up; the green LED 130C turns on when the detector detects that the wire has entered; the green LED 130C turns off when the detector detects the wire exit; the red LED 130B blinks if the guidewire comes out the wrong direction (meaning a possible situation of a catheter pulling off the guidewire and the guidewire having been left in the body); and the red LED 130B turns off when wire exits out the correct direction.

In a fifth embodiment, the fourth embodiment is further configured with a blue LED 130A such as shown in FIG. 4A. In such a configuration, the blue LED 130A illuminates when both ends of the wire exit out the correct direction in the correct order—signifying everything is good. This would stay on until the battery dies many hours later allowing visual confirmation at any time later. (If needed, screwing the cap off and then back on could reset the detector.)

Alternatively, the detector 100 can detect whether a guidewire already in a patient is properly inserted and removed from the catheter. In such a situation, when the catheter is initially placed on the caregiver-side of the guidewire and advanced toward the patient (for insertion of the catheter into the patient), the detector detects the location of the guidewire during its progress. For example, the detector detects when the caregiver-side the guidewire first enters into the detector (as detected by a first sensor at a first location). The detector then detects whether caregiver-side of the guidewire passes all the remaining sensors and whether the patient-side end of the guidewire passes each of the sensors too—indicating that the guidewire has been properly removed.

Figure 4D:
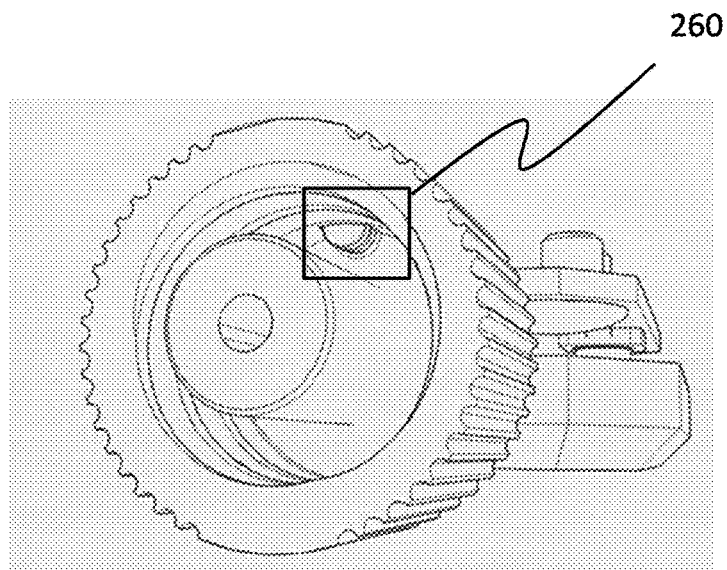
FIG. 4D is a front view of the detector of FIG. 4A where the switch activator can been seen.
Figure 4E:
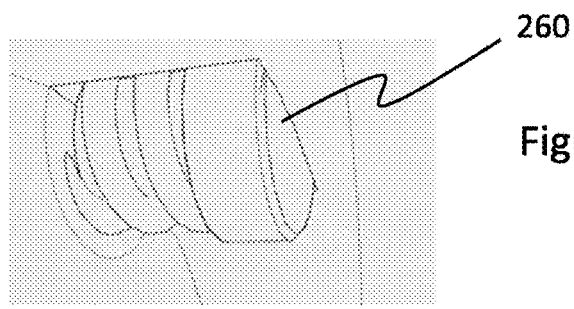
FIG. 4E is an enlarged view of the switch activator (e.g., a spring surrounding a plunger) shown within the cap of FIG. 4D.
Figure 4F:
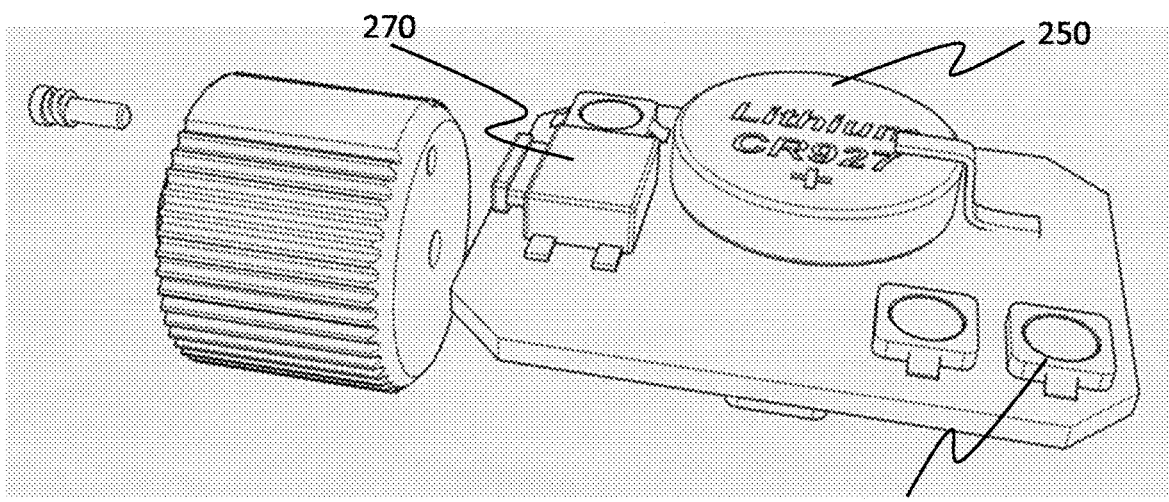
FIG. 4F is a partial exploded view of the detector (including separated cap and spring plunger system for additional clarity) of FIG. 4A to show the inter-relationship between the spring plunger system, the cap and the circuit board switch of the detector.
Figure 4G:
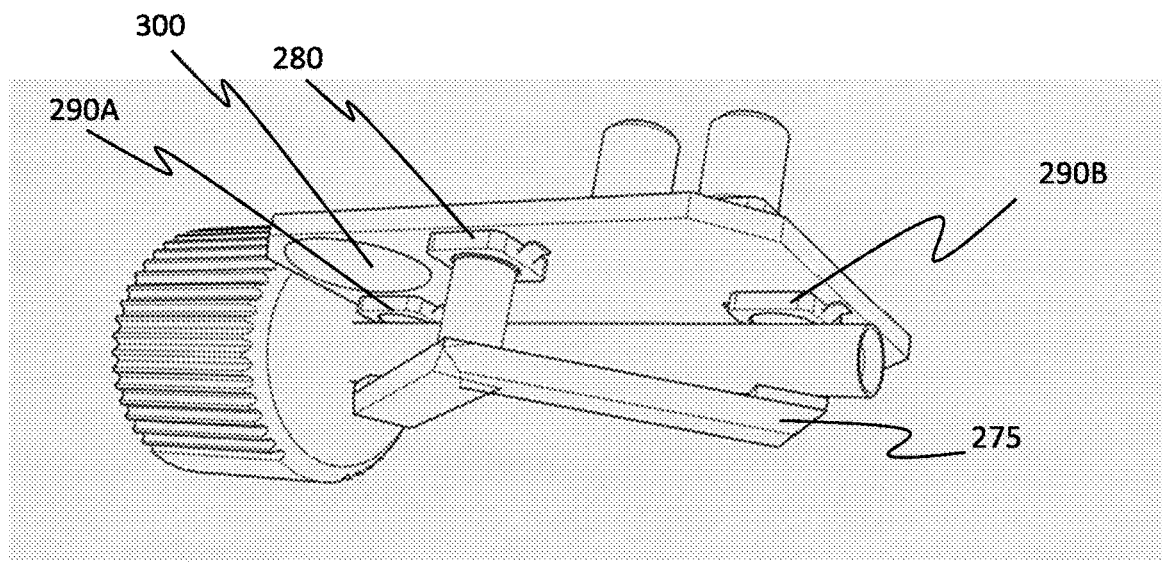
FIG. 4G is a partial underside view of the detector (showing a light transmitter, a light guide and two light detectors) of FIG. 4A to show the inter-relationship between the light transmitter, the light guide and the two light detectors and the controller mounted on the circuit board of the detector)
Figure 4H:
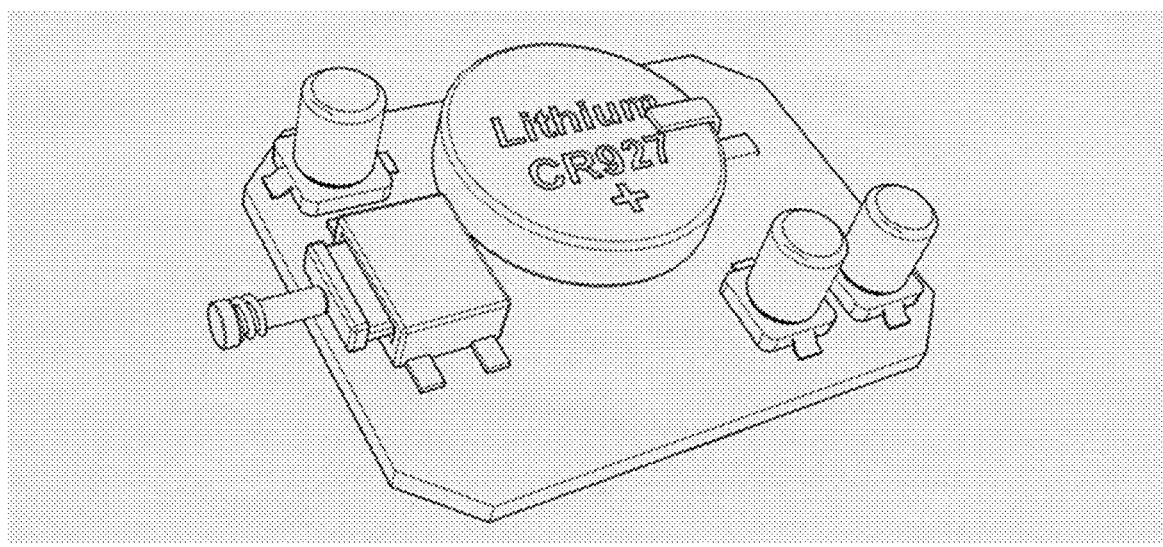
FIG. 4H is a partial exploded view of the upper portion of the circuit board of the detector when the spring plunger system abuts the switch mounted to the circuit board of the detector.
Figure 4I:
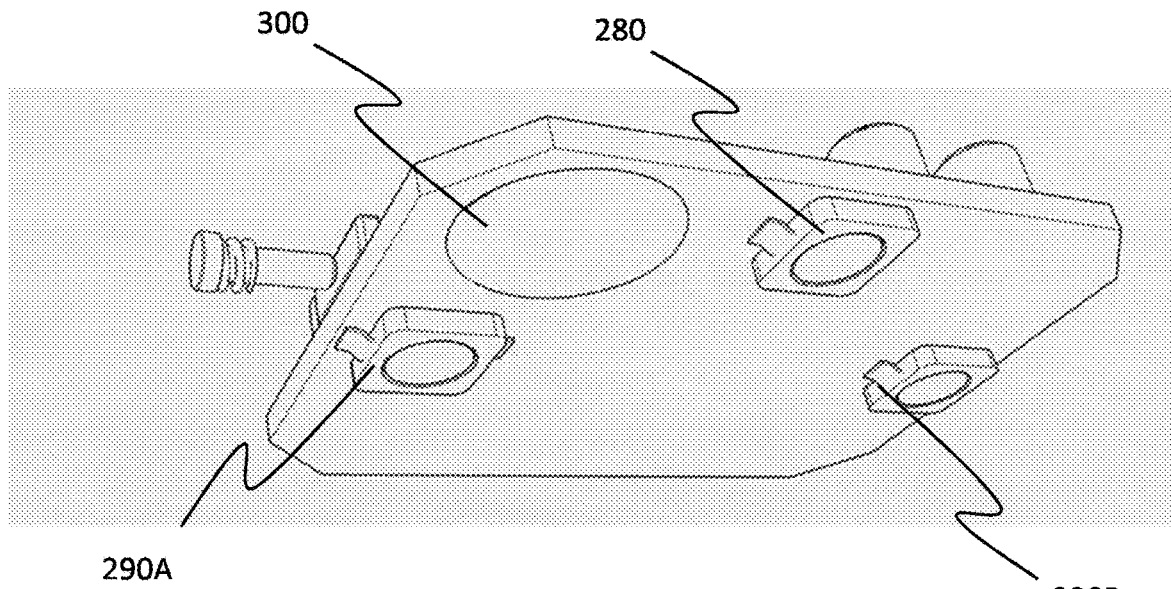
FIG. 4I is a partial underside view of the detector showing the light transmitter and the two light detectors mounted to the underside of the circuit.
Figure 4J:
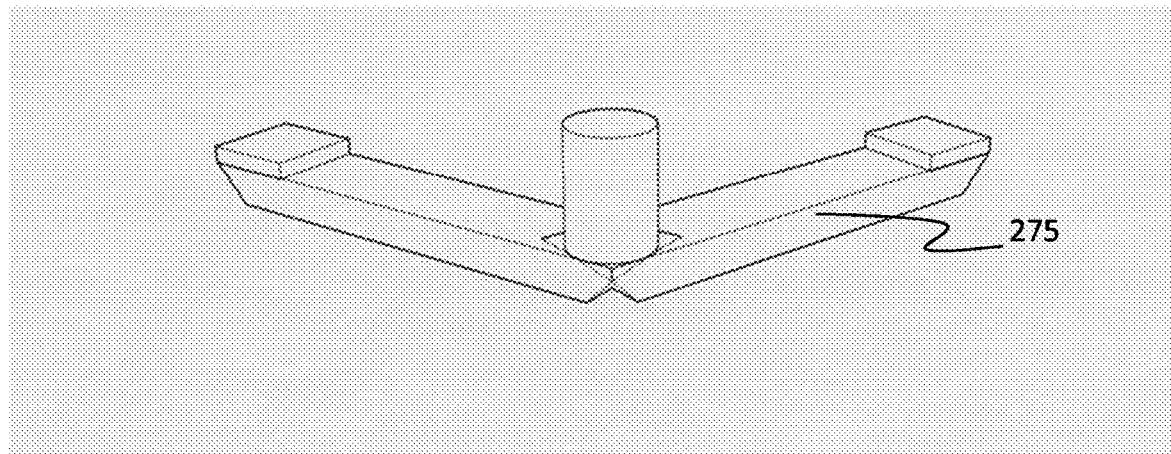
FIG. 4J is an enlarged view of the light guide and the two light detectors of FIG. 4B.

One illustrative configuration of the internal components of the detector 100 of FIG. 4A is shown in FIGS. 4B-4J. In addition to the components of the detector 100 discussed above with respect to FIG. 4A, the internal components within the housing 120 (formed from an upper shell portion 125A and a lower shell portion 125B which may snap together or be screwed together) include: (a) surface mounts LED 135A, 135B, and 135C, (b) a guidewire passage tube 200 that connects (e.g., using a friction fit) to the cap 110 and is concentric with the guidewire passage 115, (c) light sensors 210A and 210B, (d) light tube 220, (e) battery 250, (f) spring system 260, (g) switch 270, (h) light guide 275, (i) light transmitter 280 (FIG. 4G), (j) light detectors 290A and 290B (FIG. 4G), and (k) a controller 300 (e.g., die-bonded to the pc board and covered by an epoxy dot) (FIG. 4G). The battery 250 is preferably a lithium coin battery as shown. Most lithium coin cell batteries lose less than 3% of their energy each year in standby, thus giving it an excellent shelf life. The 30 mAh of energy of a CR927 is anticipated to power such a detector 100 for many hours longer than would be needed for a typical catheter insertion during surgery. As used herein, "guidewire passage tube" should be understood to include shapes other than cylindrical. The tube may, for example, have a rectangular external cross-section where it meets the light detectors to better allow the transfer of the light from the LEDs in the direction toward the light detectors. The controller 300 may be any one or a combination of: an application specific integrated circuit (ASIC), a one-time programmable logic array (e.g., a PLD using fuses), a reprogrammable logic array (e.g., a field programmable gate array (FPGA), a generic array of logic (GAL), or a logic array programmed using electrically erasable memory, flash memory, ferroelectric memory, random access memory, and/or static random access memory), and a digital computer processor with memory (including memory internal to the processor, such as electrically erasable memory, flash memory, ferroelectric memory, random access memory, and/or static random access memory, as well as memory external to the processor including electrically erasable memory, flash memory, ferroelectric memory, random access memory, and/or static random access memory).

Figure 6:
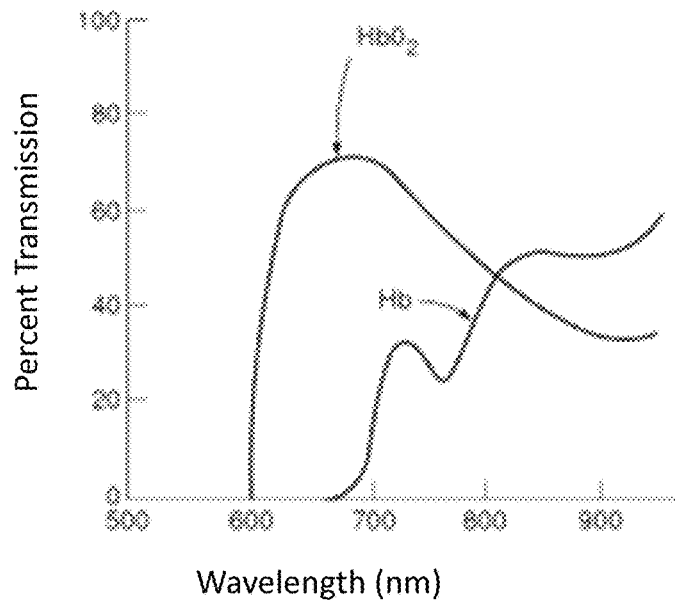
FIG. 6 is a graph showing the spectral characteristic of blood.

The detector 100 can utilize a number of different guidewire sensor systems for detecting the location and/or direction of the guidewire relative to the detector 100. In a first configuration of the guidewire sensor system, the sensing is accomplished by turning on (or pulsing it at a high rate) the light transmitter 280 (e.g., a red LED). The light from the light transmitter 280 is passed through the light tube 220 and into the light guide 275 and directed at two or more points on a guidewire passage tube 200 (e.g., a clear plastic or glass tube) running substantially the length (in the direction of motion of the guidewire) of the detector (e.g., half-an-inch apart) and coincident with the path of the guidewire. In the illustrated configuration, there are two light detectors 290A and 290B on the bottom side of the circuit board which can see the light of the light transmitter 280 having traveled along the light guide 275. Using a red LED light transmitter 280, the light detectors 290A and 290B would detect a portion of the red light having passed through the guidewire passage tube 200 when no guidewire is present in the guidewire passage tube 200. However, when the guidewire is blocking the transmissions—the intensity drops significantly allowing the corresponding light detector 290A and/or 290B to know the guidewire is at that location. Because the light detectors 290A and 290B (and potentially additional light detectors) are separated by distances sufficient to detect a moving guidewire, the sensor system can detect not only the presence of the guidewire but its direction of travel as well. Any color light may work, but preferably light in the 630 nm to 700 nm range is used because this shade of red transmits well through blood with little (or at least manageable) attenuation by the blood, as shown in FIG. 6. In general, blood looks red because it absorbs the frequencies of visible light corresponding to all of the colors except red. Therefore, red light passes through the thumb easily. Green light, however, is pretty much completely absorbed.

Figure 7:
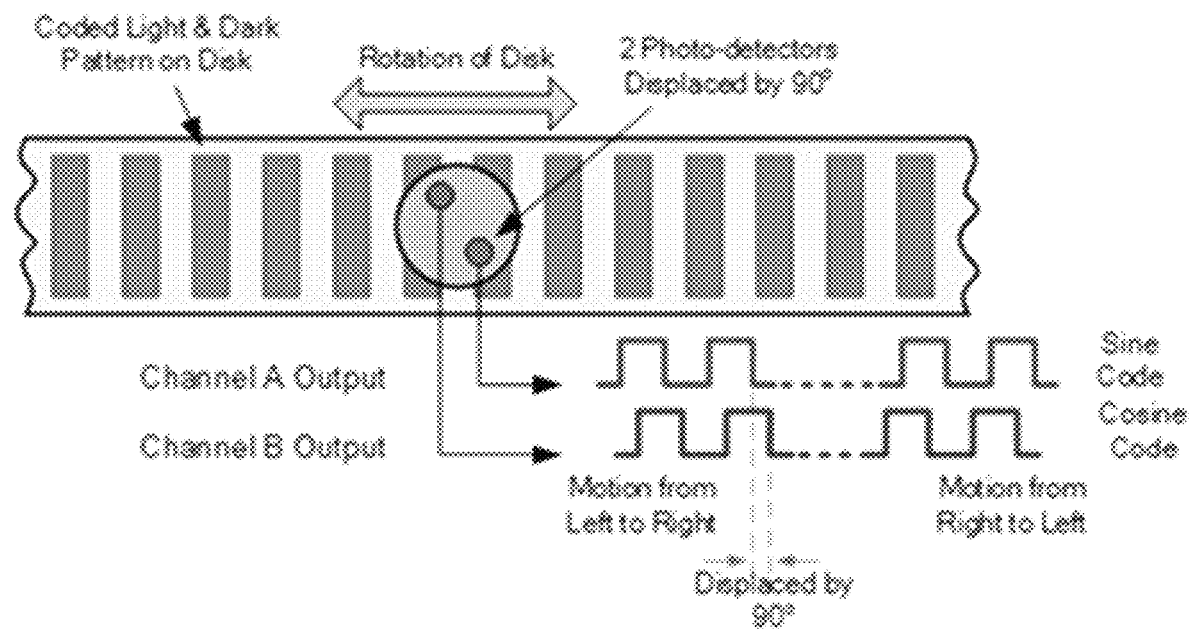
FIG. 7 is a block diagram of a simple encoder.

Alternate sensor systems also can be used. In one alternate configuration, the guidewire is in the form of steel spring. Thus, a magnetic field would be disturbed if it moved between a magnet and a sensor using a magnetometer or linear Hall effect device. Alternatively, a series of repeating bars (or other optical codes) can be printed on the wire and detected by an encoder as the wire moves by a corresponding set of sensors (as shown in FIG. 7). By using standard mathematical functions, the distance the wire has traveled—as well as the direction can be calculated. By using two offset sensors, the direction of travel is determined by noting which channel produces an output first. In yet another configuration, any other reflective method (using light, acoustic or other waves) can be used to detect the presence of the guidewire.

In one configuration, the detector 100 is powered on by screwing the cap 110 onto the port (thereby compressing the spring plunger system 260 and causing the distal end thereof to contact and activate the switch 270). FIG. 4D shows a front view of the cap 110 with the spring plunger system 260 protruding there through. FIG. 4E shows the enlarged portion of FIG. 4D that corresponds to the spring system 260 protruding through the cap 110. FIG. 4F shows an exploded view of the detector 100 where the spring system 260 has not yet been placed within the cap 110.

In yet another embodiment, a guidewire with a series of bumps at known (e.g., regular or irregular) distances is used with the detector. The detector in such a configuration utilizes a sensor that detects the bumps (e.g., by detecting a decreased amount of light as the bump passes the sensor or using at a narrow internal portion having at least one strain gauge that flexes due to contact with the bumps). The detector can count the bumps to determine how far the guidewire moves in each direction. In one such configuration, two closely spaced detectors are used to determine a direction of the guidewire based on the relative order in which the strain gauges are activated. By using a known correlation between the number of bumps, the detector can display to a medical professional how far the guidewire has been inserted into the patient and how much it has been "backed up" as it is being pulled out.

As shown in FIGS. 8A-8D, a detector having two internal sensors can determine the status of the guidewire relative to the sensors of the detector 100 attached to or integrated with the catheter. Starting with step S800 in FIG. 8A, when the detector 100 is initially powered on, the detector 100 starts in state $00_b$ (that is 00 in binary), where the more significant bit corresponds to the caregiver-side and the less significant bit corresponds to the patient-side. For each of the steps described below, the sensor detects the presence of the guidewire at its location by a "1" signal and indicates the absence of sensing the guidewire at its location by a "0" signal. As would be appreciated by those of skill in the art, the reverse polarity for the signals could be used as well. Moreover, although the discussion below assumes two sensors in the detector 100, additional sensors can be utilized to be able to detect where within the detector an end of the guidewire is located. Each sensor would then have a corresponding state bit. For example, assuming the most significant bit corresponds to the caregiver-side and the least significant bit corresponds to the patient-side, a state of $1100_b$ would represent that the patient-side end of the guidewire is half way into the detector, a state of $0011_b$ would represent that the caregiver-side end of the guidewire is half way into the detector, a state of $0000_b$ would represent that no portion of the guidewire is in the detector yet (or anymore), and a state of $1111_b$ would represent that there is guidewire at each of the sensor locations.

After control passes from Step S800 (where the initial state of the LED(s) is turned on), control passes to step S805 where a first sensor detects if there is a change in the state of the caregiver-side (from no guidewire present to guidewire present). If not, then control passes to step S810 where a second sensor detects if there is a change in the state of the patient-side (from no guidewire present to guidewire present). If not, then control returns to step S800 (or to step S805 if the LEDs do not need to be refreshed).

If step S810 indicates that there is a change in the patient-side sensor, then control passes to Step S815 which corresponds to State $01_b$. In that state, the detector changes the LED(s) to indicate (e.g., using a Yellow LED and turning off the Green LED) that the guidewire has entered from the patient-side and is expected to be pulled out the caregiver-side after the catheter has been inserted into the patient. The discussion of guidewire entering from the patient-side and that is to be pulled out the caregiver-side after the catheter has been inserted into the patient will be now provided with respect for FIGS. 8A and 8B. However, had step S805 detected a change first, then the detector would have processed the logic for a guidewire entering from the caregiver-side and that is both pushed in and pulled out the caregiver-side after the catheter has been inserted into the patient, as described with respect to FIGS. 8C and 8D.

Figure 8A:
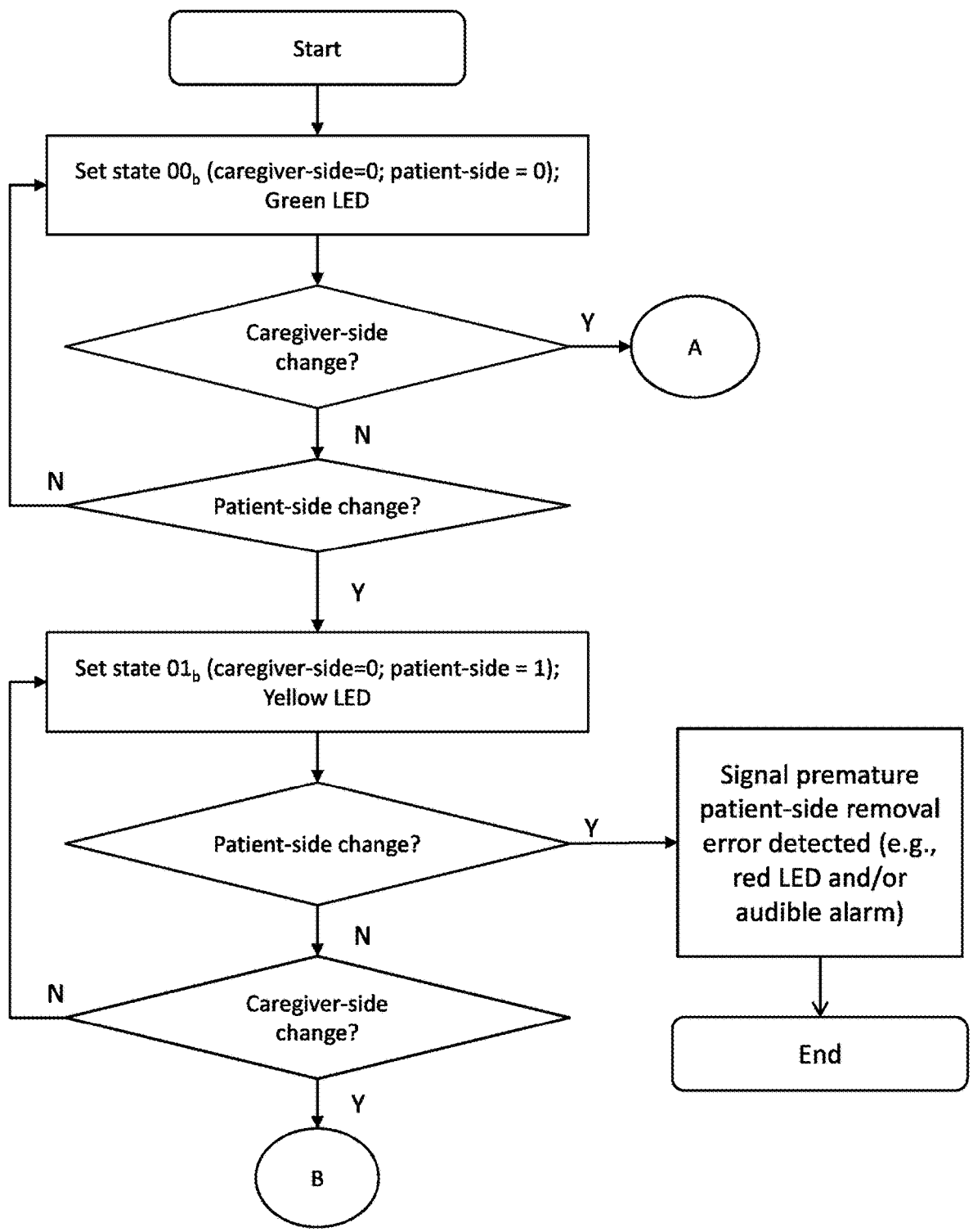
FIGS. 8A-8D combined are a flowchart showing how the detector tracks the progress of a guidewire through the detector.
Figure 8B:
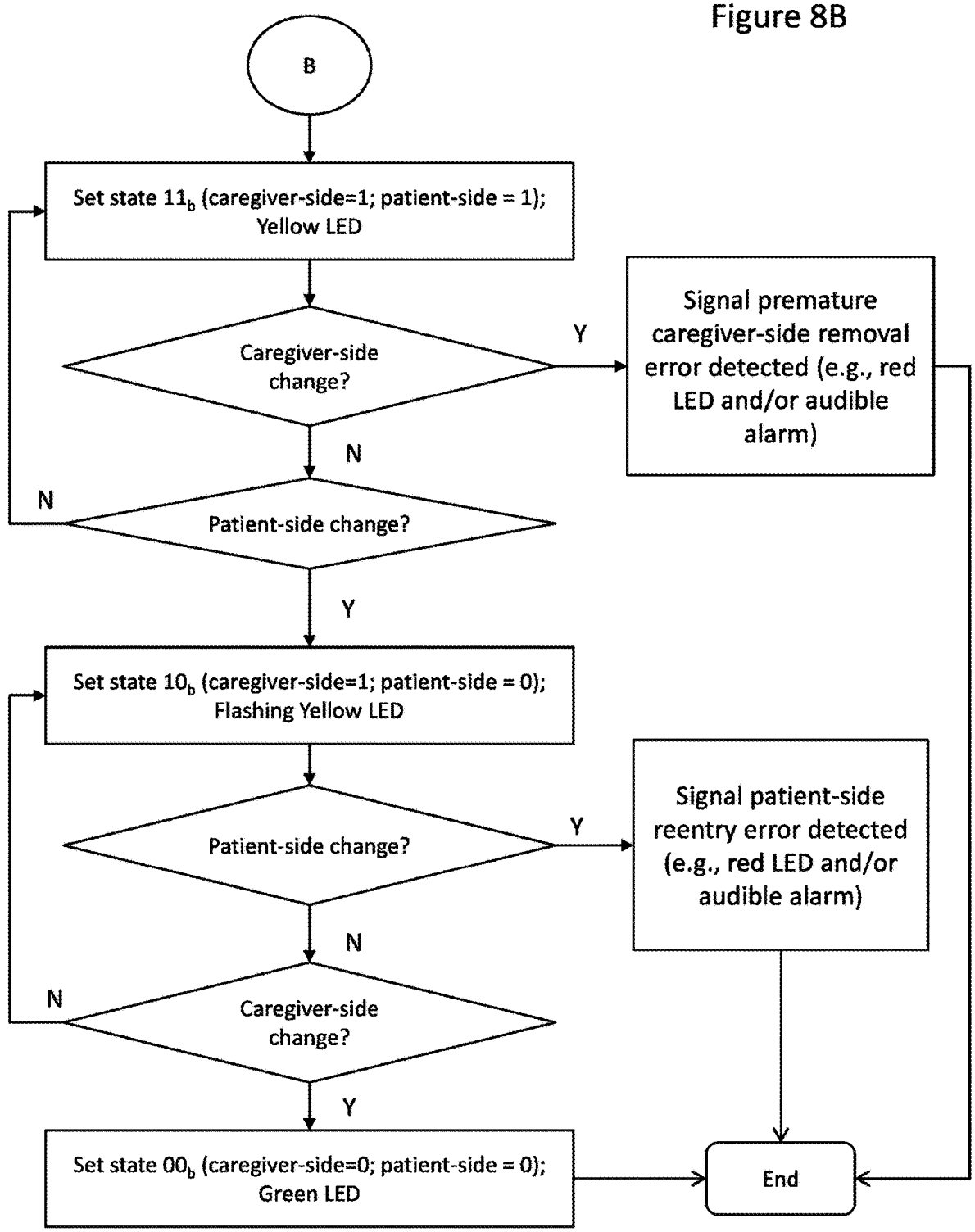

Having set itself to State $01_b$, the detector enters a loop (steps S815, S820, and S825) to determine whether there a next change detected by the sensors. If there are no changes, then the detector continues the loop (while the guidewire should be advancing toward the caregiver. If step S820 detects that the patient-side detector changes, then the guidewire has backtracked toward the patient, and control passes to step S825 where the detector signals to the caregiver that the guidewire prematurely left the patient side (e.g., by utilizing a signal via an LED or audibly). The caregiver may have intended this if the guidewire became caught, and the caregiver may silence the alarm using a reset button (not shown) such that the detector returns to its previous corresponding state (i.e., State $01_b$ for step S825). If instead step S830 detects that the guidewire has advanced to the caregiver-side, then control passes to step S835 (FIG. 8B). In step S835, the detector sets its state to State $11_b$ (corresponding to the patient-side and caregiver-sides both detecting the presence of the guidewire). The detector can further provide visual feedback (e.g., by setting an LED) or audio feedback to let the caregiver know how far the guidewire has progressed (or the LED can remain in the same illumination condition as in the previous state).

From step S835, the detector again enters a loop (S835, S840, and S850) where it waits for a change in one of the detectors. If step S840 determines that there is a change in the caregiver-side detector, the control passes to step S845 to enable the detector to alert the caregiver that the guidewire reversed back towards the patient. The caregiver may have intended this if the guidewire became caught, and the caregiver may silence the alarm using a reset button (not shown).

If instead step S850 detects that the guidewire has advanced so that it is no longer present on the patient side, then the caregiver has inserted the catheter into the patient and has begun the process of removing the wire. As such, control passes to step S855. In step S835, the detector sets its state to State $10_b$ (corresponding to only the caregiver-side detector detecting the presence of the guidewire). The detector can further provide visual feedback (e.g., by setting an LED to flashing Yellow instead of solid yellow, or by setting the LED to fast flashing yellow instead of slow flashing yellow in State $11_b$) or audio feedback to let the caregiver know how far the guidewire has progressed (or the LED can remain in the same illumination condition as in the previous state).

From step S855, the detector again enters a loop (S855, S860, and S870) where it waits for a change in one of the detectors. If step S860 determines that there is a change in the patient-side detector, the control passes to step S865 to enable the detector to alert the caregiver that the guidewire reversed back towards the patient. The caregiver may have intended this if the guidewire became caught, and the caregiver may silence the alarm using a reset button (not shown).

If instead step S870 detects that the guidewire has advanced so that it is no longer present on the caregiver side, then the caregiver has removed the guidewire from the patient. As such, control passes to step S875. In step S875, the detector sets its state to State $00_b$. The detector provides visual feedback (e.g., by setting an LED to Green) and/or audio feedback to let the caregiver know the guidewire has been successfully removed.

Figure 8C:
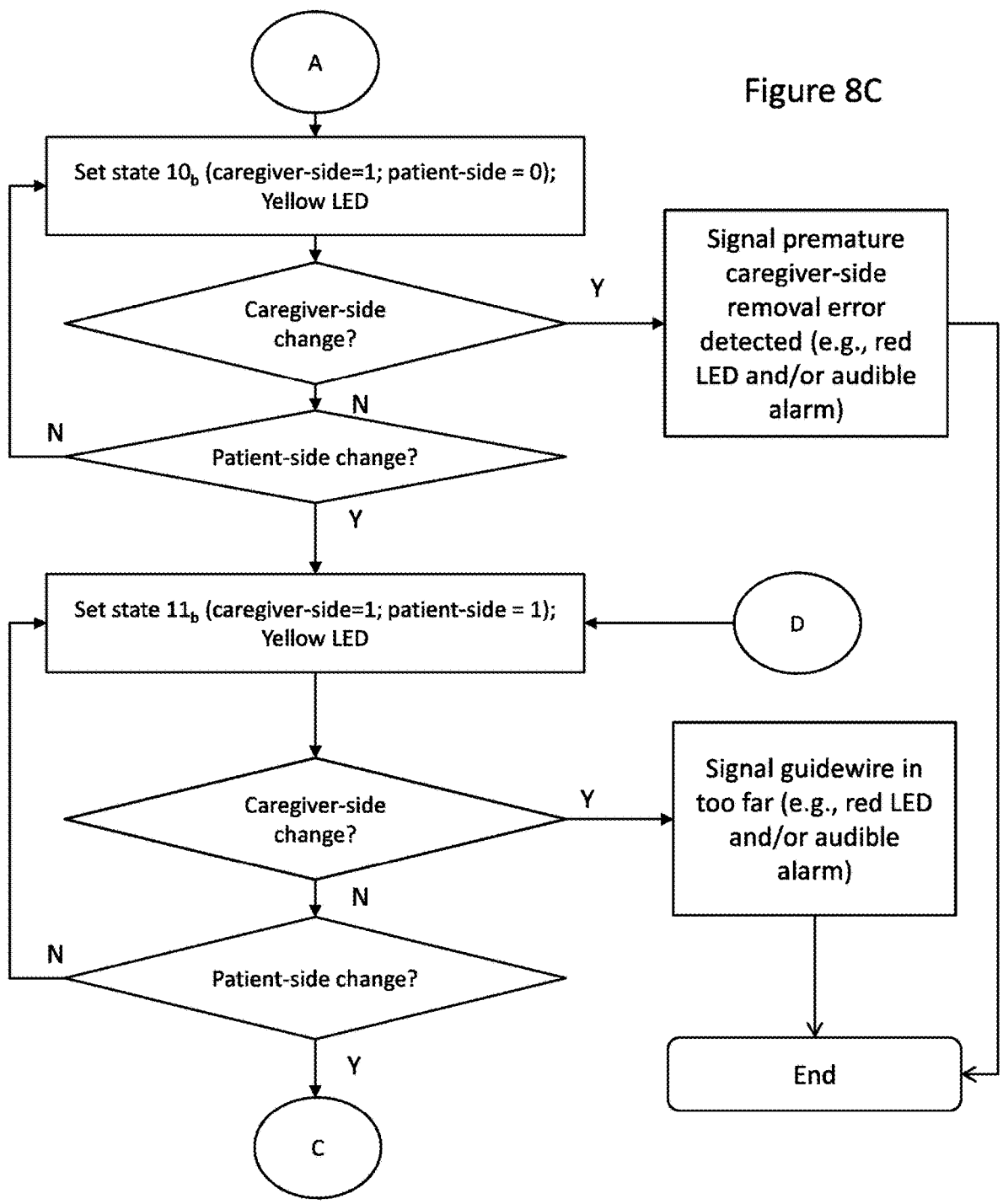
Figure 8D:
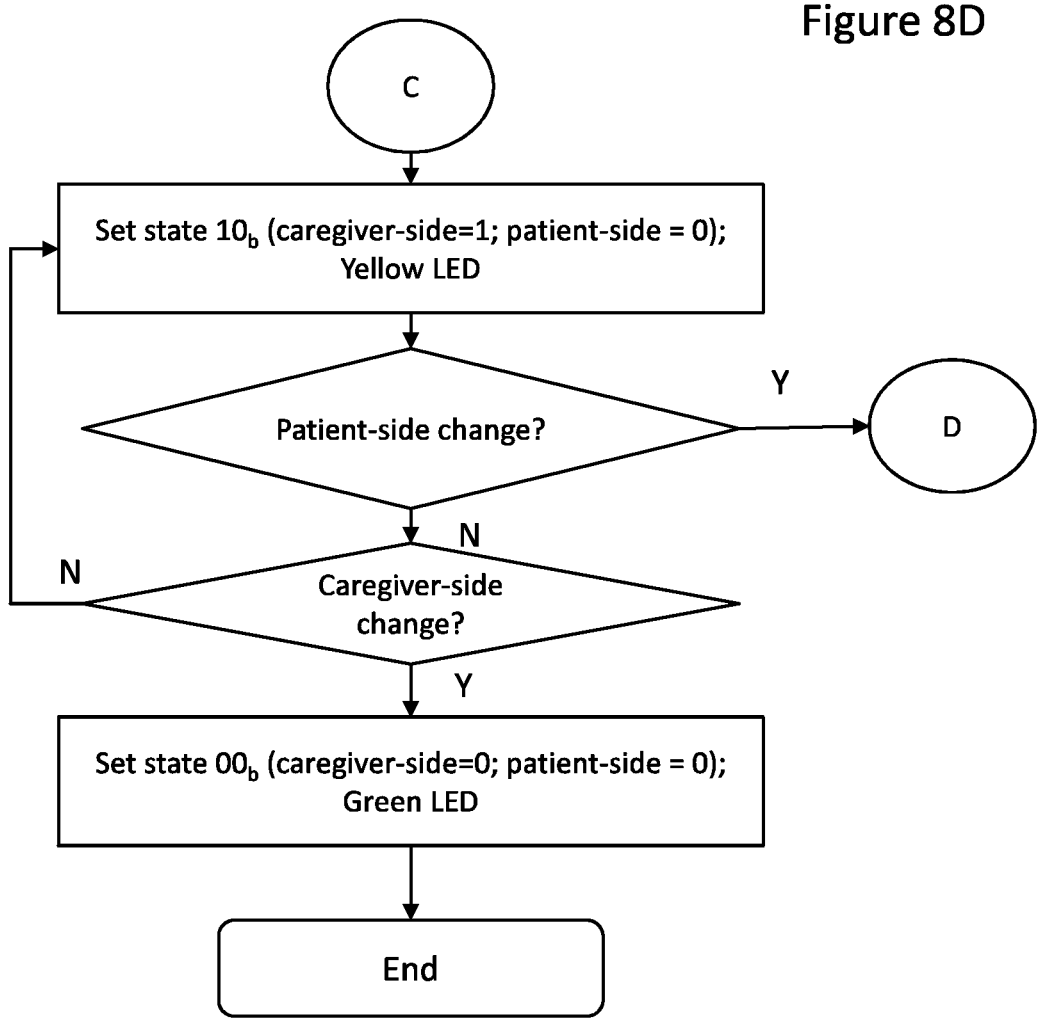

As discussed above, if step S805 detected a change in the caregiver-side before a change in the patient side, then the detector processes the logic for a guidewire entering from the caregiver-side that is both pushed in and pulled out the caregiver-side after the catheter has been inserted into the patient, as described with respect to FIGS. 8C and 8D. Similar to the steps described with respect to FIGS. 8A and 8B, the steps of FIGS. 8C and 8D perform a series of loops (loop1: S880, S885, and S900; loop2: S905, S910, and S920; and S925, S930, and S935). The logic is expecting to find that the guidewire progresses from the caregiver side, past the patient side and into the patient, and then is removed from the patient, clearing the patient-side detector and then clearing the caregiver-side detector before signaling that the catheter has been properly removed from the patient. If an unexpected change in guidewire location is determined in step S885, then the detector can alert the caregiver and the caregiver can signal if it was intended (e.g., because of a caught guidewire).

However, if step S910 detects that the guidewire has cleared the caregiver-side, then an alarm is indicated to let the caregiver know that it has lost the caregiver end of the wire and that corrective action is immediately needed. As discussed above, to further aid in preventing the guidewire from going too far into the patient, the detector may include a grabbing mechanism (e.g., a spring-loaded pinching device or a metal that changes shape when electricity is applied to it) that can be triggered to attempt to "grab" the guidewire before it is no longer within the detector. Such a grabbing device may be placed inside the tube in which the guidewire is passing or adjacent to the tube but having sufficient force to alter the shape of the tube such that the guidewire is grabbed.

As shown in step S930, it is possible that the caregiver must back the guidewire out to past the patient-side detector because the guidewire got caught but that the caregiver is going to try again. So, control can pass from step S930 to S905 without causing an alarm. In at least one alternate configuration, the steps S825, S845, S865, and S890 could have performed the same process of returning to the proper previous corresponding state without raising an alarm (assuming that the caregiver intended to partially retract the guidewire). Once the guidewire is removed past the caregiver-side detector, control passes to step S940 which indicates that the guidewire was successfully removed.

While certain configurations of structures have been illustrated for the purposes of presenting the basic structures of the present invention, one of ordinary skill in the art will appreciate that other variations are possible which would still fall within the scope of the appended claims.

The invention claimed is:

1. A detector for a guidewire to be used with a catheter, comprising:
a housing including a passageway having a first opening on a patient side of the housing and a second opening on a caregiver side of the housing; and
circuitry contained within the housing for detecting and indicating: (1) that a first end of the guidewire has not yet entered the housing through the first opening on the patient side, (2) that the first end of the guidewire has entered the housing through the first opening on the patient side and a second end of the guidewire has not passed through the second opening on the caregiver side and (3) that the second end of the guidewire has been removed from the housing through the second opening on the caregiver side having previously entered through the first opening on the patient side.

2. The detector as claimed in claim 1, further comprising:
at least one LED, wherein the circuitry for indicating: (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side comprises circuitry for illuminating the at least one LED to indicate: (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side.

3. The detector as claimed in claim 1, further comprising:
first and second LEDs, wherein the circuitry for indicating: (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side comprises:

circuitry for illuminating the first LED to indicate that the first end of the guidewire has entered the housing through the first opening on the patient side;

circuitry for illuminating the second LED to indicate that the second end of the guidewire has been removed from the housing through the second opening on the caregiver side having previously entered through the first opening on the patient side.

4. The detector as claimed in claim 1, further comprising:
a speaker, wherein the circuitry for indicating: (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side comprises circuitry for playing at least one sound through the speaker to indicate: (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side.

5. The detector as claimed in claim 4, wherein the circuitry (a) plays the at least one sound to indicate that the second end of the guidewire has entered the housing through the first opening on the patient side and (b) stops playing the at least one sound to indicate that the second end of the guidewire has been removed from the housing through the second opening on the caregiver side having previously entered through the first opening on the patient side.

6. The detector as claimed in claim 4, wherein the circuitry (a) periodically plays the at least one sound to indicate that the first end of the guidewire has entered the housing through the first opening on the patient side and (b) stops periodically playing the at least one sound to indicate that the second end of the guidewire has been removed from the housing through the second opening on the caregiver side having previously entered through the first opening on the patient side.

7. The detector as claimed in claim 1, further comprising a guidewire passage tube, wherein the circuitry for detecting and indicating comprises a light transmitter for transmitting light at a selected frequency and first and second light detectors to detect (1) that the guidewire is blocking light from the light transmitter from reaching the first light detector and (2) that the guidewire is blocking light from the light transmitter from reaching the second light detector.

8. The detector as claimed in claim 7, wherein the selected frequency is in the 630 nm to 700 nm range.

9. The detector as claimed in claim 1, wherein the circuitry comprises an application specific integrated circuit (ASIC).

10. The detector as claimed in claim 1, wherein the circuitry comprises a one-time programmable logic array.

11. The detector as claimed in claim 1, wherein the circuitry comprises a reprogrammable logic array.

12. The detector as claimed in claim 1, wherein the circuitry comprises and a digital computer processor with non-transitory computer memory for storing instructions, wherein the digital computer processor is controlled by computer instructions read from the non-transitory computer memory.

13. The detector as claimed in claim 1, further comprising:
a cap connected to the housing;
a spring system integrated with the cap; and
a switch configured to contact the spring system when the cap is connected to a catheter port, wherein the switch powers on the circuitry when the cap is connected to a catheter port.

14. The detector as claimed in claim 1, further comprising at least two optical sensors spaced apart, wherein the circuitry for detecting and indicating comprises circuitry configured to determine a direction of movement of the guidewire using the at least two optical sensors.

15. A detector for a guidewire to be used with a catheter, comprising:
a housing including a passageway having a first opening on a patient side of the housing and a second opening on a caregiver side of the housing; and
circuitry contained within the housing for detecting and indicating: (1) that the guidewire has not yet entered the housing, (2) that the guidewire has entered the housing, (3) that the guidewire has been removed from a patient through the housing, and (4) determine a distance a first end of the guidewire has progressed past the detector housing having exited the first opening while moving in a direction from the second opening to the first opening.

16. The detector as claimed in claim 15, wherein the guidewire is marked along its length with color bands or marked with magnetic energized bands, and
wherein the detector further comprises a sensor system configured to determine the distance the guidewire has progressed past the detector housing into the patient.

17. The detector as claimed in claim 16, wherein at least one of an LCD display, a 7-segment display, and a display is configured to show the distance the guidewire that has progressed past the detector housing into the patient.

18. A method of detecting a state of a guidewire being placed into a catheter connected to a detector having a housing including a passageway having a first opening on a patient side of the housing and a second opening on a caregiver side of the housing, the method comprising:
powering on the detector prior to a first end of the guidewire entering the first opening on the patient side by at least one of attaching the detector to the catheter and pushing a power button on the detector;
indicating using the detector that the first end of the guidewire has not yet entered the housing through the first opening on the patient side;
detecting and indicating using the detector that the first end of the guidewire has entered the housing through the first opening on the patient side and a second end of the guidewire has not passed through the second opening on the caregiver side; and detecting and indicating using the detector that the second end of the guidewire has been removed from the housing through the second opening on the caregiver side having previously entered through the first opening on the patient side.

19. The method as claimed in claim 18, wherein, using at least one LED, the detector indicates (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side.

20. The method as claimed in claim 18, wherein, using at least one speaker, the detector indicates (1) that the first end of the guidewire has not yet entered the housing through the first opening on the patient side, (2) that the first end of the guidewire has entered the housing through the first opening on the patient side and the second end of the guidewire has not passed through the second opening on the caregiver side and (3) that the second end of the guidewire has been removed from the housing through the second opening on the caregiver side having previously entered through the first opening on the patient side.

21. The method as claimed in claim 18, further comprising:
    transmitting, using a light transmitter, light at a selected frequency; and
    detecting, using first and second light detectors, (1) that the guidewire is blocking light from the light transmitter from reaching the first light detector and (2) that the guidewire is blocking light from the light transmitter from reaching the second light detector.

* * * * *